(12) United States Patent
Chen et al.

(10) Patent No.: US 6,913,582 B2
(45) Date of Patent: Jul. 5, 2005

(54) UNIVERSAL HAND SPLINT

(75) Inventors: Franklin Chen, Edison, NJ (US); Jeffrey Stearns, Hopatcong, NJ (US)

(73) Assignee: EBI, L.P., Parsippany, NJ (US)

( * ) Notice: Subject to any disclaimer, the term of this patent is extended or adjusted under 35 U.S.C. 154(b) by 142 days.

(21) Appl. No.: 10/352,261

(22) Filed: Jan. 27, 2003

(65) Prior Publication Data

US 2004/0147862 A1 Jul. 29, 2004

(51) Int. Cl.[7] .................................................. A61F 5/00
(52) U.S. Cl. ............................ 602/5; 602/20; 602/21; 602/22; 128/878; 128/879
(58) Field of Search .................. 128/878, 879, 128/880, 881; 602/5, 20, 21; 2/16, 19, 20, 161.1

(56) References Cited

U.S. PATENT DOCUMENTS

| | | | | |
|---|---|---|---|---|
| 2,958,325 A | 11/1960 | Claydon et al. | ............. | 128/90 |
| 3,703,894 A | 11/1972 | Galloway et al. | ............. | 128/77 |
| 3,788,307 A | 1/1974 | Kistner | ......................... | 128/77 |
| 4,013,070 A | * 3/1977 | Harroff | ......................... | 128/77 |
| 4,103,682 A | 8/1978 | Franzl | ......................... | 128/87 |
| 4,716,892 A | * 1/1988 | Brunswick | ................... | 128/77 |
| 4,782,825 A | 11/1988 | Lonardo | ......................... | 128/77 |
| 4,813,406 A | 3/1989 | Ogle, II | ........................ | 128/87 |
| 4,840,168 A | 6/1989 | Lonardo | ..................... | 128/77 |
| 4,873,968 A | * 10/1989 | Finnieston | ................ | 128/87 R |
| 5,058,576 A | 10/1991 | Grim et al. | ............... | 128/87 R |
| 5,113,849 A | 5/1992 | Kuiken et al. | ................ | 128/26 |
| 5,417,645 A | * 5/1995 | Lemmen | ....................... | 602/21 |
| 5,637,078 A | 6/1997 | Varn | ........................... | 602/21 |
| 5,652,955 A | 8/1997 | Skewis | ........................... | 2/20 |
| 5,672,150 A | 9/1997 | Cox | ............................ | 602/21 |
| 5,722,092 A | * 3/1998 | Borzecki | ......................... | 2/16 |
| 5,772,620 A | * 6/1998 | Szlema | ........................ | 602/21 |
| 6,013,044 A | 1/2000 | Estwanik | ..................... | 602/64 |
| 6,063,087 A | 5/2000 | Agee et al. | ................... | 606/55 |
| 6,106,492 A | 8/2000 | Darcey | .......................... | 602/8 |
| 6,120,471 A | 9/2000 | Varn | ........................... | 602/21 |
| 6,165,148 A | 12/2000 | Carr-Stock | .................. | 602/21 |
| 6,200,286 B1 | 3/2001 | Zamani | ....................... | 602/64 |
| 6,293,919 B1 | 9/2001 | Manente | ...................... | 602/21 |

* cited by examiner

Primary Examiner—Michael A. Brown
(74) Attorney, Agent, or Firm—Harness, Dickey & Pierce, P.L.C.

(57) ABSTRACT

A gutter splint aids the healing of injuries to the metacarpals, proximal phalanges, and middle phalanges by substantially immobilizing the injured digits. The splint includes a volar member and a dorsal member. The volar member has a volar forearm support region for supporting a volar forearm, a volar palm support region for supporting a palm of the hand at a predetermined angle to the forearm, and a finger support region for supporting the fingers at a predetermined angle to the palm. The dorsal member has a dorsal forearm support region for supporting the dorsal forearm, a dorsal hand support region for supporting the hand at a predetermined angle to the dorsal forearm, and a finger support region for supporting the fingers at a predetermined angle to the dorsal hand. The volar member and dorsal member are flexibly secured to each other using a series of removable straps.

8 Claims, 5 Drawing Sheets

UNIVERSAL HAND SPLINT

FIELD OF THE INVENTION

The present invention generally relates to orthopedic hand splints useful in facilitating healing of an injured hand. In particular, the present invention relates to a universal hand splint that aids healing of an injured hand through immobilization of the hand and select fingers.

BACKGROUND OF THE INVENTION

Orthopedic splints commonly referred to as "gutter" splints are conventionally used to facilitate healing of injured bones. Gutter splints are useful because they immobilize injured bones, thus allowing the bones to heal quickly and in the proper orientation. While a variety of gutter splints currently exist for treating bone injuries of the hand and wrist area, such conventional gutter splints are not particularly useful in facilitating the healing of injuries to the metacarpals, proximal phalanges, and middle phalanges. Specifically, conventional gutter splints are either not capable of adequately immobilizing injured digits and/or exhibit one or more of the below described deficiencies.

Conventional gutter splints are difficult to manufacture and apply. Specifically, most conventional gutter splints must be custom made by a physician or a hand therapist using plaster, fiberglass, or thermoplastic. This process is tedious and inefficient. Additionally, conventional gutter splints cannot be inelastically deformed to meet the needs of specific patients. Thus, there is a need for a pre-fabricated, universally sized, and easy to apply hand splint that is capable of immobilizing injured digits.

Many conventional hand splints are further undesirable because they are bulky and uncomfortable and thus fail to promote patient compliance. If the splint is not comfortable for the patient to wear, the patient will not wear the splint and will not benefit from the healing effects associated with wearing the splint. Thus, there is a need for a hand splint that is comfortable to wear and thus promotes patient compliance.

Conventional plaster and fiberglass gutter splints are often permanently secured to the patient's arm and/or hand. Such conventional gutter splints are undesirable because they fail to provide immediate and easy access to the injured area when medically appropriate. Further, such gutter splints fail to allow removal of the splint to permit early mobilization of the injured digits as medically necessary and fail to permit removal for cleaning. Thus, there exists a need for a hand splint that can be easily secured to and detached from the bones of the patient's hand when necessary to permit access to the injured area, early mobilization of the injured digits, and cleaning of the splint.

Additional deficiencies associated with conventional gutter splints are that they are subject to being applied incorrectly and place the hand and fingers in improper positions for healing. Further, conventional gutter splints are often applied either too tightly or loosely and fail to take into account swelling of the injured area. Thus, there is a need in the pertinent art for a hand splint that insures the placement of the hand and fingers in the proper position for healing (referred to in the art as "intrinsic plus position") and may be adjustable in response to patient swelling, thus providing edema control.

SUMMARY OF THE INVENTION

The present invention overcomes the deficiencies of the prior art by providing a hand splint that aids the healing of hand injuries and particularly aids the healing of injuries to the metacarpals, proximal phalanges, and middle phalanges. The gutter splint aids the healing of the above described injuries by immobilizing the injured digits. The splint is generally comprised of a volar member and a dorsal member.

The volar member generally includes a volar forearm support region for supporting a volar forearm, a volar palm support region for supporting a palm of the hand at a first predetermined angle to the forearm, and a volar finger support region for supporting the fingers at a second predetermined angle to the palm. The dorsal member generally includes a dorsal forearm support region for supporting the dorsal forearm, a dorsal hand support region for supporting the dorsal hand at a third predetermined angle to the dorsal forearm, and a dorsal finger support region for supporting the fingers at a fourth predetermined angle to the dorsal hand. The volar member and dorsal member are flexibly secured to each other using a series of removable straps.

The use of the hand splint of the present invention is advantageous as a single size can universally fit a wide range of patients, the splint may be easily secured to and removed from the patient to permit ready access to the injured area and easy cleaning, and the splint promotes patient compliance as it is less bulky and more comfortable to wear than conventional gutter splints.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

Figure 1:
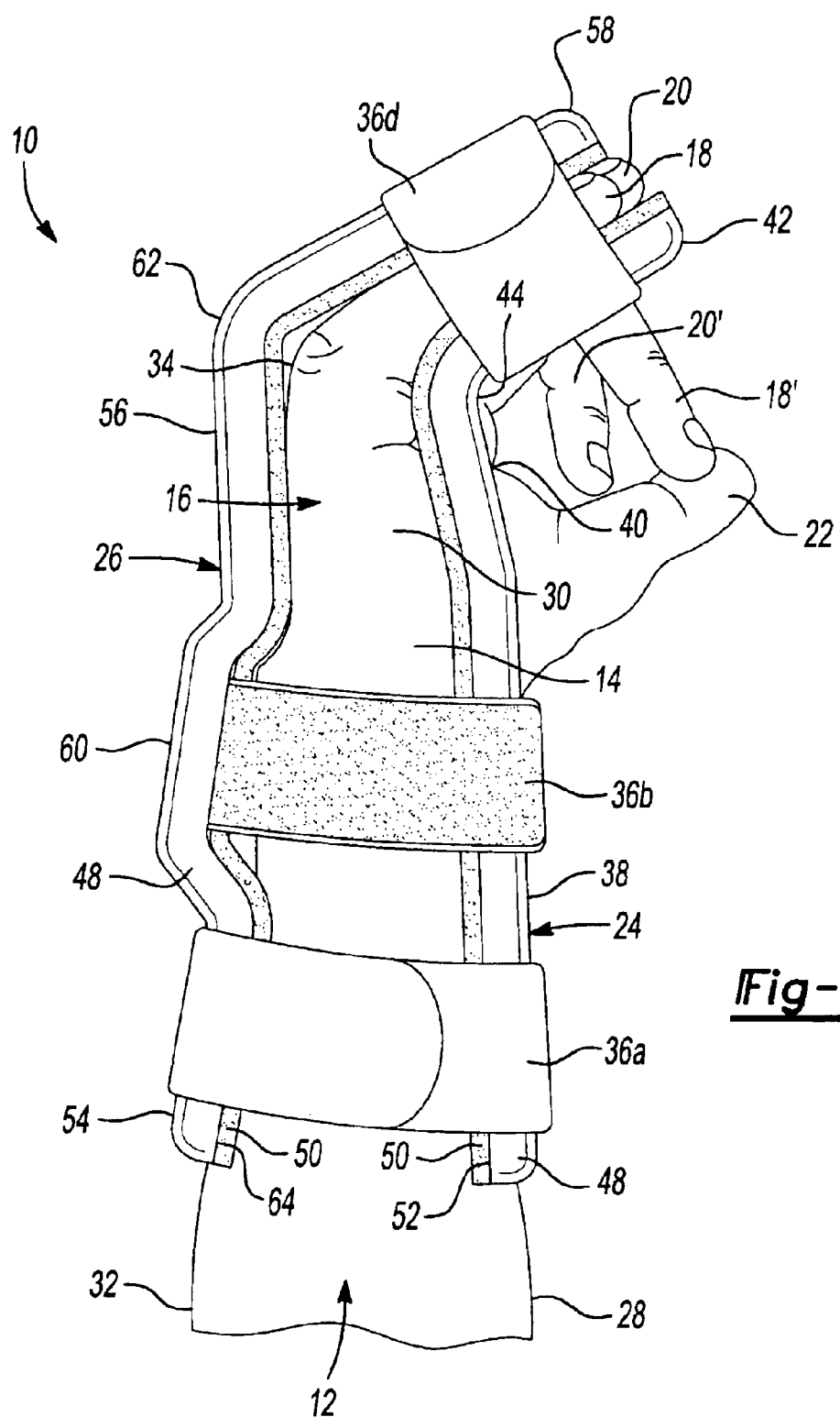
FIG. 1 is a side view of a splint assembly constructed in accordance with a preferred embodiment of the present invention, the splint assembly is shown operatively associated with a patient and functioning as a right ulnar splint assembly.

An orthopedic splint according to a preferred embodiment of the present invention is generally illustrated in FIG. 1 at 10. The splint 10 is illustrated operatively associated with a patient's forearm 12, wrist 14, and hand 16. In the particular application shown, the splint 10 is illustrated securing a first pair of fingers, such as a small finger 18 and a ring finger 20, to immobilize the ulnar aspects of a hand 16. It will become apparent to those skilled in the art, however, that the splint 10 may similarly be used to immobilize the ulnar aspects of a left hand (not shown). It will also become apparent to those skilled in the art that the splint 10 may be used to secure the index finger 18' and long finger 20' to immobilize the radial aspects of a left or right hand 16. Throughout the intended applications, the design of the splint 10 allows a thumb 22 of the hand 16 to remain flexible and avoid atrophy, even when the splint 10 is secured to the hand 16 and the fingers 18 and 20. By securing the first pair of fingers 18 and 20, the splint 10 allows the second pair of adjacent fingers 18' and 20' to be laterally spaced from the splint 10 for freedom of movement. In FIG. 1, the second pair of fingers 18' and 20' are shown partially bent for better clarity in the view of FIG. 1.

With continuing reference to FIG. 1 and additional reference to FIGS. 2 through 6, the construction of the splint 10 will now be described in further detail. The splint 10 is preferably a gutter splint and is illustrated to generally include a first or volar member 24 and second or dorsal member 26. In use, the volar member 24 is positioned adjacent a volar side 28 of the forearm 12, the wrist 14, and a palm 30 of the hand. The volar member 24 extends from a first or proximal end of the splint 10 to a second or distal end of the splint 10 at or near the ends of the fingers 18 and 20. The dorsal member 26 is positioned adjacent a dorsal side 32 of the forearm 12, the wrist 14 and a dorsal member 34 of the hand 16. The dorsal member 26 similarly extends from the first or proximal end of the splint 10 to a second or distal end of the splint 10 at or near the tips of the fingers 18 and 20. Both the volar member 24 and the dorsal member 26 are fastened to each other, and the forearm 12, the wrist 14, the hand 16, and the fingers 18 and 20, using a plurality of straps 36 or other suitable fastening arrangement. The straps 36 allow for flexible interconnection of the volar and dorsal members 24 and 26 and are described in further detail below.

The volar member 24 generally includes a volar forearm support region 38, a palm support region 40, and a volar finger support region 42. The different support regions 38, 40, and 42 generally support the body parts after which they are named. Specifically, the forearm support region 38 abuts and provides support to the volar forearm 28. The palm support region 40 abuts and provides support to the palm 30. The finger support region 42 abuts and supports the volar side of the fingers 18 and 20.

The forearm support region 38 is substantially planar so as to correspond with the substantially planar volar forearm 28. The palm support region 40 is also substantially planar but is angled inward, towards the palm 30, to support the hand 16 at an angle for healing. The angle of the palm support region 40 in relation to the forearm support region 38 may be any suitable angle for properly positioning the hand 16 for healing. In one particular application, the palm support region 40 is positioned relative to the forearm support region 38 at a predetermined angle of approximately 10 degrees.

Extending from the palm support region 40 is the finger support region 42. The finger support region 42 is substantially planar and is angled in the opposite direction of the palm support region 40 (i.e. back towards the forearm support region 38). The angle of the finger support region 42 in relation to the palm support region 40 may be any suitable angle for properly positioning the fingers 18 and 20 for healing. In the embodiment illustrated, the finger support region 42 is positioned relative to the palm support region 40 at a predetermined angle of approximately 70 degrees. Between palm support region 40 and finger support region 42 is a transition 44. The transition 44 is preferably rounded to correspond to the position of the hand 16 as supported by the volar member 24.

Figure 5:
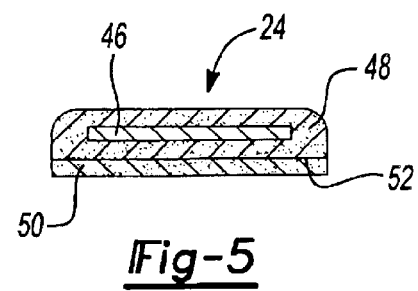
FIG. 5 is a cross-sectional view taken along the line 5—5 of FIG. 4.

As shown most clearly in the cross-sectional view of FIG. 5, the volar member 24 is constructed to include a rigid member or backbone 46. The backbone 46 extends substantially the entire length of the volar member and is preferably manufactured of a rigid metal or other suitable material. Surrounding the metal backbone 46 is a soft padded material 48, such as a closed cell foam. In the embodiment illustrated, the volar member 24 of the splint 10 further includes an open cell foam layer 50 for positioning adjacent the skin of the patient for enhanced comfort. The open cell foam layer 50 is glued or otherwise suitably fastened to an interior side 52 of the volar member 24. Alternatively, the open cell foam layer 50 can be eliminated in favor of closed cell foam.

The dorsal member 26 of the splint 10 will now be described in detail. The dorsal member 26 generally includes a dorsal forearm support region 54, a dorsal hand support region 56, and a dorsal finger support region 58. As with the volar member 24, the different support regions 54, 56, and 58 of the dorsal member 26 generally support the body parts for which they are named. Specifically, the dorsal forearm support region 54 abuts and provides support to the dorsal forearm 32. The dorsal hand support region 56 abuts and provides support to the dorsal hand 34. The dorsal finger support region 58 abuts and provides support to the dorsal side of the fingers 18 and 20.

The positions of the three support regions 54, 56, and 58 of the dorsal member 26 generally mirror the three support regions 38, 40, and 42 of the volar member 24. Specifically, the dorsal forearm support region 54 is of a length substantially identical to the volar forearm support region 38. However, unlike the volar forearm support region 38, the dorsal forearm support region 54 includes an offset region 60.

The offset region 60 is generally positioned over the wrist 14. The offset region 60 provides additional clearance between the dorsal member 26 and the wrist 14. Thus, the offset region 60 provides clearance for the ulnar styloid to allow the splint to fit more intimately and comfortably. In general, the offset region 60 expands the number of patients that may be outfitted with the splint 10.

The dorsal hand support region 56 is substantially planar but is angled away from the dorsal forearm support region 54 to support the hand 16 at a proper angle for healing. The angle of the dorsal hand support region 56 may be any suitable angle for properly positioning the hand 16 for healing. In the embodiment illustrated, the dorsal hand support region 56 is angled at approximately 15 degrees to the dorsal forearm support region 54.

Extending from the dorsal hand support region 56 is the dorsal finger support region 58. The dorsal finger support region 58 is substantially planar and is angled in the opposite direction of the dorsal hand support region 56. The angle of the finger support region 58 in relation to the dorsal hand support region 56 may be any suitable angle for properly positioning the fingers 18 and 20 for healing. In the embodiment illustrated, the finger support region 58 is positioned relative to the dorsal hand support region 56 at a predetermined angle of approximately 70 degrees. Connecting the hand support region 56 to the finger support region 58 is a transition region 62. The transition region 62 is preferably curved to correspond to the position of the hand 16 as supported by the dorsal member 26.

The composition of the dorsal member 26 is substantially similar to the composition of the volar member 24. Specifically, the dorsal member 26 includes a rigid member or backbone (not shown). The backbone is preferably manufactured of a rigid metal. Surrounding the metal backbone is the soft padded material 48. In the embodiment illustrated, the dorsal member 26 is illustrated to further include the layer 50 of open cell foam for positioning adjacent the skin. The open cell foam layer 50 is glued or otherwise suitably fastened to an interior side 64 of the dorsal member 26. Again, the open cell foam layer 50 can be eliminated in favor of closed cell form.

The plurality of straps 36a–d will now be further described. A first strap 36a is preferably non-elastic and secures the volar forearm support region 38 and the dorsal forearm support region 54 to the forearm 12. Specifically, the first strap 36a is anchored to the dorsal forearm support region 54 by a fastening mount 66. The fastening mount 66 is rigidly secured to the dorsal forearm support region 54. Seated on top of the mount 66 is a fastening region 68. In the embodiment illustrated, the fastening region 68 is a first dorsal hook component 68 of a hook and loop type fastening system. The hook component 68 interacts with a corresponding loop component 70 (FIG. 2) located on an interior of the first strap 36a. The hook component 68 releasably and securely receives the loop component 70 after the strap 36a is wrapped around the forearm 12 and corresponding volar forearm support region 38. Such hook and loop type fastening systems are commercially available under the trademark Velcro®. While this type of fastening is preferred for its ease of use, other manners of fastening may be employed within the scope of the present invention.

To enhance the ability of the first strap 36a to secure the volar forearm support region 38 and the dorsal forearm support region 54 to the forearm 12, an additional fastening region, in the form of a volar forearm hook component 72, is located on the forearm support region 38 of the volar member 24. The forearm hook component 72 receives the loop component 70 of the strap 36a to secure the strap 36a to the volar member 24.

A second strap 36b is preferably inelastic and secures the offset region 60 to the forearm support region 38. The second strap 36b is secured to an inner side of the dorsal member below the open cell form 50 with a suitable anchoring device (not shown). A loop 74 (FIG. 6) formed from an end of the second strap 36b extends from a side of the offset region 60 opposite the side from which a free end of the second strap 36b extends. The loop 74 is coupled to a buckle 76. The buckle 76 receives the free end of the strap 36b after the strap 36b is wrapped around the wrist 14 and the forearm support region 38. Once the strap 36b is received by the buckle 76, the strap 36b is folded back upon itself and fastened to itself through interaction between a hook component 78 located at a terminus of the strap 36b and a loop component 80 located on a body of the strap 36b. While this type of fastening system is preferred for its ease of use, other manners of fastening may be employed within the scope of the present invention.

A third strap 36c permanently secures the volar member 24 to the dorsal member 26. The third strap 36c is fixedly secured to the volar member 24 at the volar finger support region 42 beneath a volar finger support region fastening mount 82. The third strap 36c is fixedly secured to the dorsal member 26 at the dorsal finger support region 58 beneath a dorsal finger support region fastening mount 84. The third strap 36c is preferably a flexible elastic strap to permit the easy insertion of the fingers 18 and 20 between the volar member 24 and the dorsal member 26.

Figure 2:
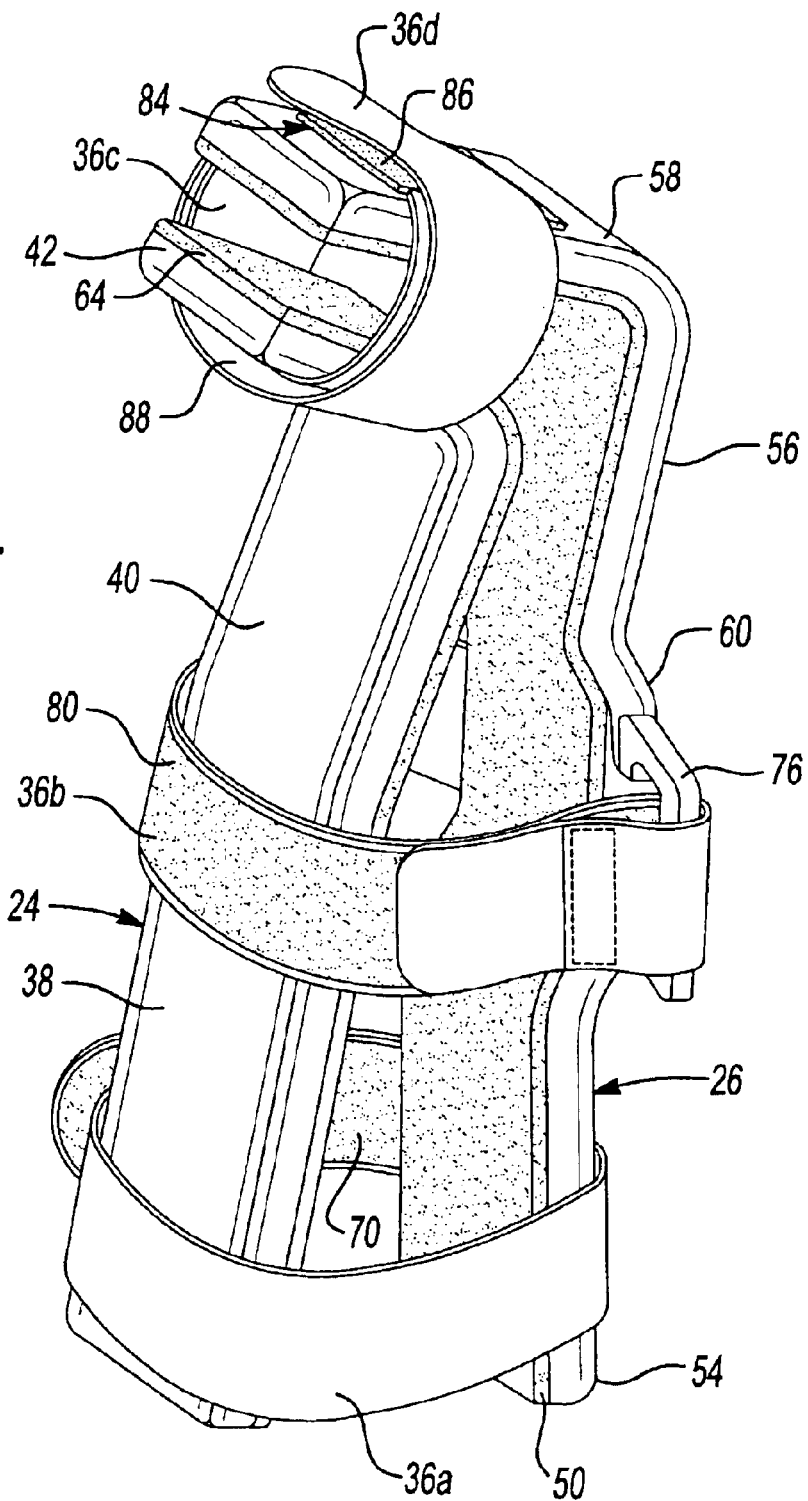
FIG. 2 is a perspective view of the splint assembly of the preferred embodiment of the present invention.
Figure 3:
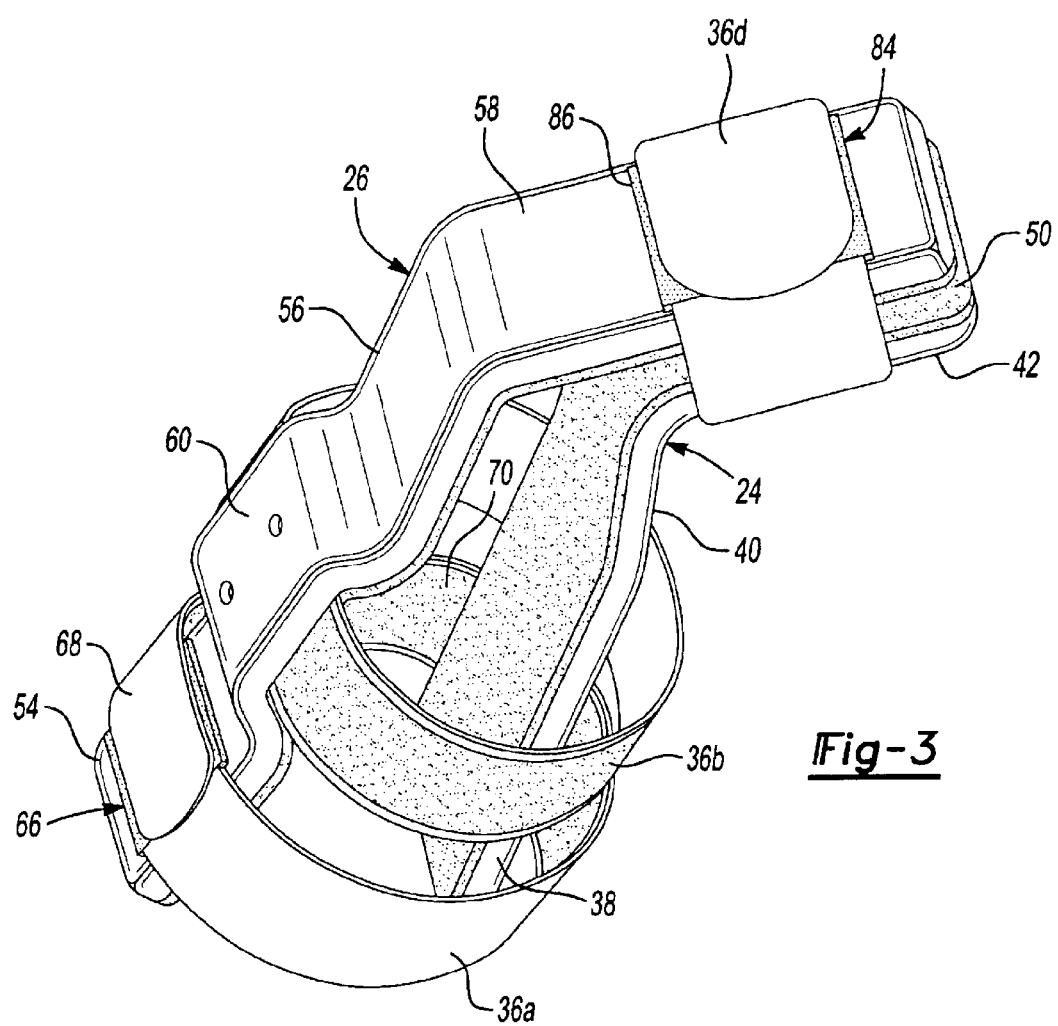
FIG. 3 is an additional perspective view of the splint assembly of the preferred embodiment of the present invention.

A fourth strap 36d adjustably secures the volar finger support region 42 to the dorsal finger support region 58. The fourth strap 36d is fixedly secured to the dorsal finger support region 58 by the dorsal finger support region fastening mount 84. Seated atop the fastening mount 84 is a hook component 86 of a hook and loop type fastening system, commercially available under the trademark Velcro®. The hook component 86 cooperates and secures a corresponding loop component 88 located on an interior surface of the fourth strap 36d after the fourth strap 36d is wrapped around the fingers 18 and 20 and the finger support region 42. To enhance the ability of the fourth strap 36d to secure the volar finger support region 42 to the dorsal finger support region 58, as the strap 36d is wrapped around the volar finger support region 42, the loop component 88 is fastened to a corresponding hook component 90 (FIG. 4) seated atop the volar finger support region fastening mount 82. The fourth strap 36d is wrapped over and around the elastic strap 36c as illustrated in FIG. 2.

Figure 4:
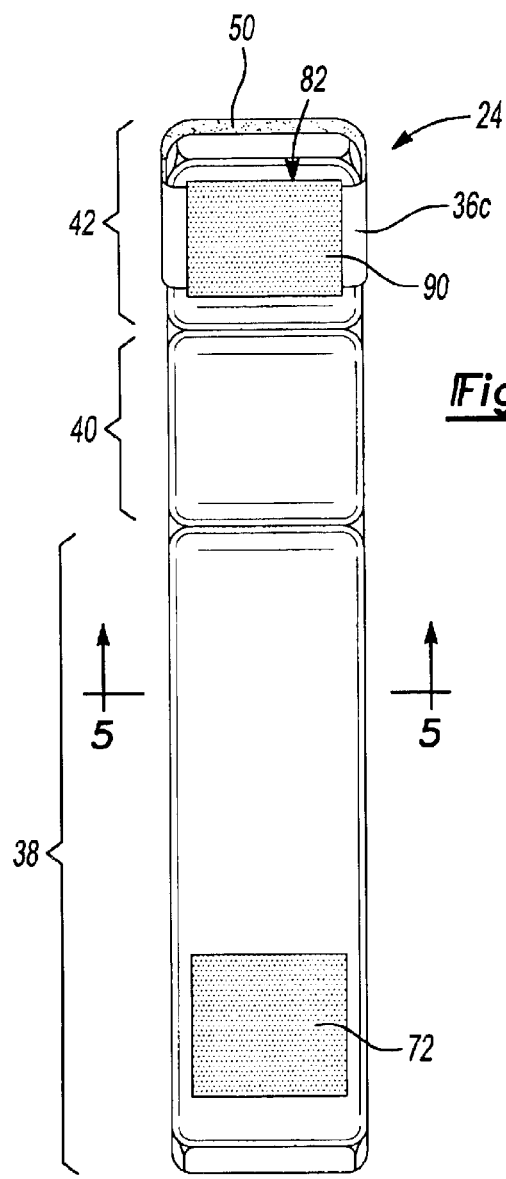
FIG. 4 is a bottom view of the volar member of the splint assembly of the preferred embodiment of the present invention.
Figure 6:
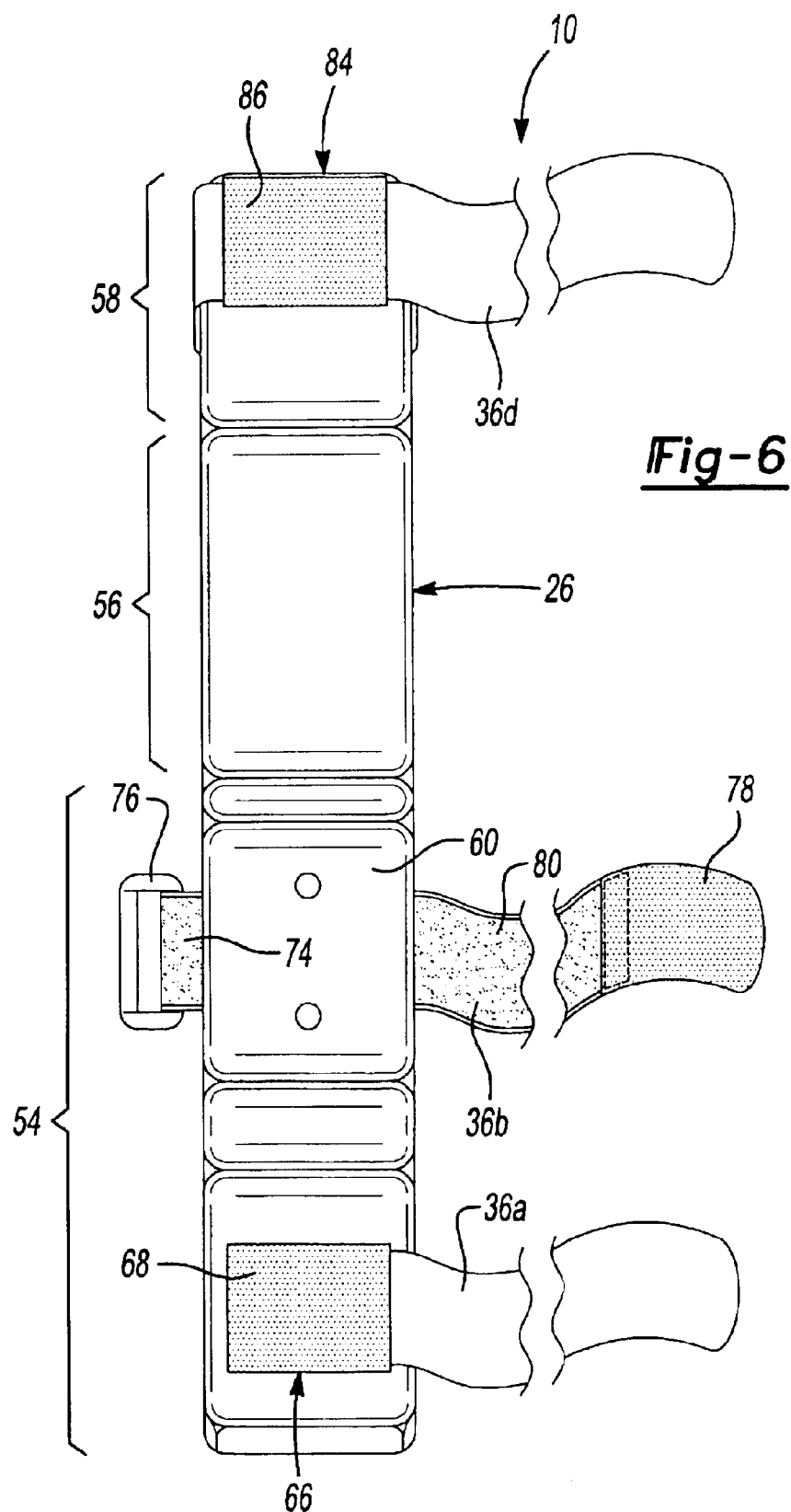
FIG. 6 is a top view of the splint assembly of the preferred embodiment of the present invention.

The use of the splint 10 will now be described in detail. Before the splint 10 is applied to the patient, the straps 36a, 36b and 36d are preferably placed in a loosened position (FIGS. 2 and 3) or are completely disengaged from interaction with the volar member 24 (FIGS. 4 and 6). Once the straps 36a, b and d are properly positioned or opened, the patient inserts his or her forearm 12, wrist 14, and hand 16 between the volar member 24 and the dorsal member 26, as seen in FIG. 1. The volar member 24 is preferably positioned such that the transition 44 between the palm support region 40 and the volar finger support region 42 is in close proximity to a base of proximal phalanges 92. Once the transition 44 is properly positioned, the other regions of the volar member 24 fall into proper alignment with the fingers 18 and 20 extending to near the terminus of the finger support region 42 and the forearm support region 38 extending down the volar forearm 28.

The dorsal member 26 is preferably positioned such that the transition 62 between the dorsal hand support region 56 and the dorsal finger support region 58 is generally over knuckles 94. Once the transition 62 is properly positioned, the other regions of the dorsal member 26 fall into proper position. Specifically, the dorsal finger support 58 is positioned so that it extends approximately the length of the fingers 18 and 20 and the dorsal forearm support region 54 extends down the dorsal forearm 32.

Once the volar member 24 and the dorsal member 26 are properly positioned, the straps 36a, 36b, and 36d are tightened to securely fasten the splint 10 to the forearm 12, wrist 14, hand 16, and fingers 18 and 20. Specifically, strap 36a, which extends from the mount 66, is wrapped around the forearm 12 and the volar member 24 and secured to the hook components 68 and 72 through interaction between the loop component 70 and the hook components 68 and 72.

The strap 36d is inelastic strap substantially similar to the strap 36a. The strap 36d extends from fastening mount 84 and is wrapped around the dorsal finger support region 58 and the volar finger support region 42. The strap 36d is secured in position through interaction between the loop component 88 and the two separate hook components, specifically hook component 86 which is mounted on fastening mount 84 as shown in FIG. 2 and hook component 90 which is mounted on fastening mount 82 as shown in FIG. 4.

To secure the strap 36b to the wrist 14, the strap 36b is wrapped around the wrist 14 and the volar member 24 and then subsequently threaded through buckle 76. After threading buckle 76, the strap 36b is then folded back upon itself such that the hook component 78 engages the loop component 80.

The use of straps 36a–d to secure the splint 10 the patient is advantageous for many reasons. The use of straps 36a–d permits the splint 10 to be easily and quickly secured to the patient, thus making health care personnel more efficient and permitting hand injuries to be addressed more expeditiously. Further, straps 36 allow the splint 10 to be easily detached from the patient when necessary to permit ready access to the injured area, early mobilization of the injured digits, and easy cleaning. Still further, the straps 36*a*, 36*b*, and 36*d* may be readily tightened and loosened to adjust the pressure exerted upon the injured area by the splint 10. Thus, the straps 36 provide the splint 10 with an edema control device.

Use of splint 10 is also advantageous as it eliminates the need for the manufacture of a customized splint for each patient, thus allowing the patient to be immediately outfitted with the splint 10 and reducing inventories. Specifically, a single size of splint 10 can fit a wide range of patients. Further, the use of the elastic strap 36*c* permits a secure fit for patients having finger circumferences of most any size.

Finally, the use of splint 10 is advantageous as it promotes patient compliance. If a splint is uncomfortable or bulky the patient is less likely to wear the splint and will not benefit from the healing effects provided by the splint. The splint 10 is light in weight, not bulky, and generally more comfortable to wear than existing splints. Consequently, patients are more likely to wear the splint 10 and experience the positive healing effects of the splint 10.

Thus, the present invention provides a gutter splint 10 for immobilizing an injured hand and for specifically immobilizing injured metacarpals, proximal phalanges, and middle phalanges. The splint 10 is generally comprised of a volar member 24 and a dorsal member 26. The volar member 24 is generally comprised of a volar forearm support region 38 for supporting the volar forearm 28, a volar palm support region 40 for supporting the palm 30 at a first predetermined angle to the forearm 12, and a finger support region 42 for supporting the fingers 18 and 20 at a second predetermined angle to the palm 30. The dorsal member 26 is generally comprised of a dorsal forearm support region 54 for supporting the dorsal forearm 32, a dorsal hand support region 56 for supporting the dorsal hand 34 at a third predetermined angle to the dorsal forearm 32, and a finger support region 58 for supporting the fingers 18 and 20 a fourth predetermined angle to the dorsal hand 34. The volar member 24 and dorsal member 26 are secured to each other using a series of removable straps 36*a–d*.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for selectively immobilizing a portion of injured hand of a patient, the method including the steps of:

providing a gutter splint having a volar member and a dorsal member;

positioning the volar member adjacent a volar forearm, a palm region of the hand, and a volar region of a first pair of adjacent fingers;

positioning the dorsal member adjacent a dorsal forearm, a dorsal region of said hand, and a dorsal region of the first pair of adjacent finger; and adjustably securing the volar member to the dorsal member with a fastening arrangement including at least one strap wrapped about a distal end of the volar member and a distal end of the dorsal member such that the first pair of adjacent fingers is secured therebetween and a second pair of adjacent fingers is laterally spaced from the splint for freedom of movement.

2. The method of claim 1, wherein the step of adjustably securing the volar member and the dorsal member includes the step of permanently securing the volar and dorsal members with an elastic strap adjacent a distal end of the splint.

3. The method of claim 1, wherein the step of adjustably securing includes the step of wrapping a plurality of inelastic straps around the volar and dorsal members.

4. The splint of claim 3, wherein the step of substantially immobilizing the first pair of adjacent fingers includes the step of substantially immobilizing a small finger and a ring finger.

5. The splint of claim 3, wherein the step of substantially immobilizing the first pair of adjacent fingers includes the step of substantially immobilizing a middle finger and an index finger.

6. The splint of claim 3, wherein the step of substantially immobilizing the first pair of adjacent fingers includes the step of substantially immobilizing a pair of adjacent fingers on a left hand of the patient.

7. The splint of claim 3, wherein the step of substantially immobilizing the first pair of adjacent fingers includes the step of substantially immobilizing a pair of adjacent fingers on a right hand of the patient.

8. The splint of claim 1, further comprising the step of substantially immobilizing the first pair of adjacent fingers while retaining movement of the second pair of adjacent fingers.

* * * * *